United States Patent [19]

Bruno

[11] Patent Number: 5,217,904
[45] Date of Patent: Jun. 8, 1993

[54] APPARATUS AND METHOD FOR EVAPORATIVE CONCENTRATION OF A LIQUID SAMPLE

[75] Inventor: Thomas J. Bruno, Broomfield, Colo.

[73] Assignee: The United States of America as represented by the Secretary of the Department of Commerce, Washington, D.C.

[21] Appl. No.: 819,021

[22] Filed: Jan. 10, 1992

[51] Int. Cl.$^5$ .............................................. G01N 1/22
[52] U.S. Cl. .................................... 436/181; 436/174; 422/101; 159/16.1; 159/47.1; 202/160; 202/161; 202/182; 202/185.3; 202/267.1; 203/2; 203/49; 203/81; 203/DIG. 2
[58] Field of Search ................ 436/174, 181; 422/101; 159/16.1, 47.1; 202/20, 160, 161, 182, 185.3, 267.1; 203/2, 49, 86, DIG. 2

[56] References Cited

U.S. PATENT DOCUMENTS

| | | |
|---|---|---|
| 1,651,557 | 12/1926 | Senseman .............................. 422/70 |
| 2,248,634 | 7/1941 | Krause ................................... 422/70 |
| 3,015,474 | 1/1962 | Dalin et al. ..................... 203/DIG. 2 |
| 3,956,061 | 5/1976 | Young et al. ..................... 159/48 L |
| 4,311,668 | 1/1982 | Solomon .............................. 436/177 |
| 4,333,017 | 7/1984 | O'Connell ............................. 290/2 |
| 4,427,053 | 1/1984 | Klaren ..................................... 165/1 |
| 4,472,355 | 9/1984 | Hickman et al. ..................... 422/62 |
| 4,707,452 | 11/1987 | Friswell ............................... 436/177 |
| 4,963,231 | 10/1990 | Ryham .................................... 203/22 |
| 5,084,133 | 1/1992 | Guy et al. ............................. 159/47.1 |
| 5,096,543 | 3/1992 | Elmore ................................. 202/172 |

FOREIGN PATENT DOCUMENTS 1118161 6/1968 United Kingdom .

Primary Examiner—James C. Housel
Assistant Examiner—N. Bhat
Attorney, Agent, or Firm—Holly D. Kozlowski

[57] ABSTRACT

An apparatus for evaporative concentration of a liquid sample comprises a housing including an upper chamber and a lower chamber, a concentrator flask, a reflex tube and a vortex tube. The concentrator flask includes an upper solution vessel section and a lower cold finger section, and the flask is arranged within the housing with the solution vessel section positioned in the upper chamber and the cold finger section positioned in the lower chamber. The reflex tube is arranged at the upper end of the concentrator flask. The vortex tube has a cold air outlet connected with an inlet to the lower chamber of the housing and a hot air outlet connected with an inlet to the upper chamber of the housing. The apparatus is employed to concentrate a liquid sample contained in the concentrator flask with the temperatures of the cold and hot air from the vortex tube being sufficient to induce the evaporative separation of samples.

10 Claims, 2 Drawing Sheets

APPARATUS AND METHOD FOR EVAPORATIVE CONCENTRATION OF A LIQUID SAMPLE

FIELD OF THE INVENTION

The present invention relates to an apparatus for the evaporative concentration of a liquid sample, and to a method for concentrating a liquid sample using the apparatus.

BACKGROUND OF THE INVENTION

In many synthetic and analytical procedures, it is necessary to increase the concentration of a liquid solution sample by the controlled evaporation of the solvent. One commonly employed apparatus comprises the micro or Kuderna Danish concentrators disclosed, for example, by Shugar et al, *Chemical Technicians Ready Reference Handbook*, 2nd Ed., McGraw-Hill, New York (1981). These concentrators comprise glass flasks consisting of a relatively large volume solution vessel, for example, of 10 to 100 mL, above a relatively small volume cold finger trap, for example, of 0.5 to 1 mL. A reflux condenser is positioned at the upper end of the concentrator flask by means of a ground glass joint. An electric heating unit is commonly employed with these concentrators. The heating unit consists of an aluminum block provided with one or more holes that accommodate the solution vessel section of the concentrator, leaving the cold finger section exposed to ambient air, and therefore in thermally responsive relation to the ambient air. The solution vessel is heated by the block using proportionally controlled resistive heaters to provide the desired evaporation.

These known concentrators have several serious disadvantages. First, the electrically heated aluminum block poses a safety hazard. That is, if the solvent being evaporated is flammable and has a vapor density greater than that of air, vapors can accumulate at the base of the unit and ignition can occur by arcing in the controller or switch. Thus, such a unit is not suitable for use in an explosion-proof laboratory. The concentrators are also disadvantageous in that the cold finger trap in ambient air is often warmed significantly through conduction from the heating block and conduction through the solution vessel. This heating is undesirable since the cold finger section should be maintained at a cooler temperature to minimize bumping and decomposition of sensitive solutes. This heating is further undesirable since it applies an unfavorable temperature gradient opposing thermal solute transport. Furthermore, it is difficult to observe the liquid in the solution vessel section of the concentrator while the flask is in the heating block. Accordingly, a need exists for an improved evaporative concentration apparatus for use with liquid samples.

Examples of further prior art concentrating apparatus and methods are disclosed in the Senseman U.S. Pat. No. 1,651,557, the Krause U.S. Pat. 2,248,634, the Solomon U.S. Pat. No. 4,311,668 and the Friswell U.S. Pat. No. 4,707,452. Additionally, British Patent No. 1,118,161 discloses a laboratory gas generator apparatus including a liquid container having an enlarged middle portion and a lower, open ended finger portion.

SUMMARY OF THE INVENTION

Accordingly, it is an object of the present invention to provide an apparatus for use in the evaporative concentration of a liquid sample. It is a further object of the invention to provide such an apparatus which overcomes disadvantages of prior art concentrators. It is a more specific object of the invention to provide an apparatus for the evaporative concentration of a liquid sample, which apparatus is safe and efficient in use. It is a further object to provide such an apparatus which is inexpensive and easily manufactured. It is a related object to provide a safe and efficient method for concentrating a liquid sample by evaporation means.

These and additional objects are provided by the apparatus and method of the present invention. More particularly, the present invention comprises an apparatus and method for the evaporative concentration of a liquid sample. The apparatus comprises a housing including an upper chamber and a lower chamber, a concentrator flask, a reflux tube, and a vortex tube. The concentrator flask includes an upper solution vessel section and a lower cold finger section and is arranged within the housing with the solution vessel section of the flask positioned in the upper chamber of the housing and the cold finger section of the flask positioned in the lower chamber of the housing. The reflux tube is arranged at the upper end of the concentrator flask. The vortex tube has a cold air outlet connected with an inlet to the lower chamber of the housing and a hot air outlet connected with an inlet to the upper chamber of the housing. In accordance with the method of the present invention, the temperatures of the cold air and hot air supplied by the vortex tube are sufficient to induce evaporative separation of the liquid sample and thermal concentration of the solute. Because the apparatus of the present invention does not include electrical heating means, the safety problems incurred by prior art concentrators are avoided. Additionally, the present apparatus and method provide an inexpensive yet efficient means for the evaporative concentration of liquid samples, with thermal transport of the solutes.

These and additional objects and advantages provided by the present apparatus and method will be more fully apparent in view of the following detailed description.

BRIEF DESCRIPTION OF THE DRAWING

The following detailed description may be more fully understood in view of the drawing in which.

DETAILED DESCRIPTION

Figure 1:
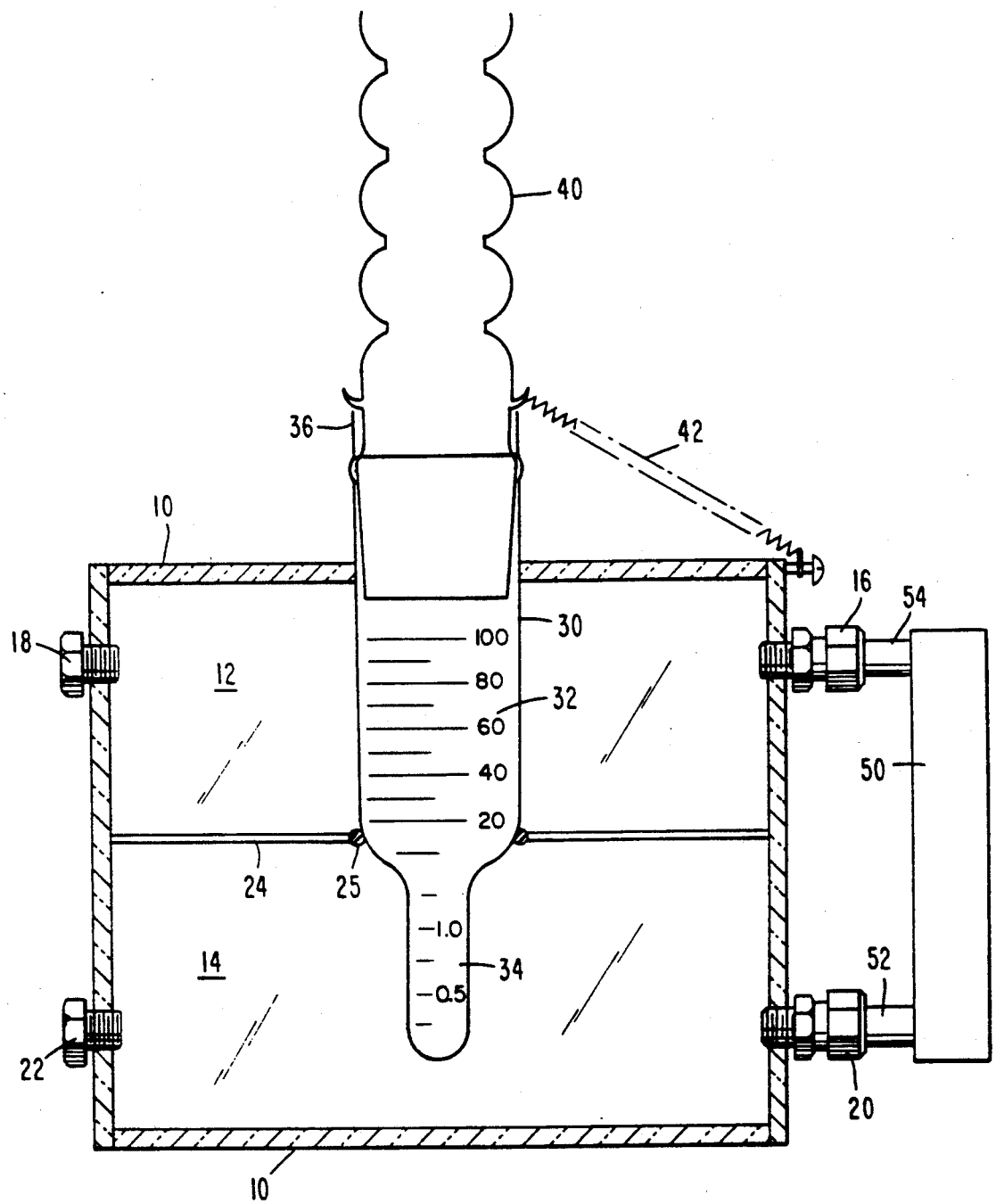
FIG. 1 comprises a schematic, partial cross-sectional drawing of an apparatus according to the present invention.

The present apparatus and method combine the use of a concentrator flask and a reflux tube as known in the prior art with a housing and a vortex tube to provide a safe and efficient but inexpensive means for concentrating a liquid sample by evaporation and thermal transport. The apparatus is shown schematically in partial cross-section in FIG. 1 and comprises a housing 10 including an upper chamber 12 and a lower chamber 14. In order that the operator of the apparatus can view the evaporation process, it is preferred that the housing 10 is constructed of a transparent material, for example, glass or a transparent plastic. A suitable plastic comprises transparent polycarbonate, available commercially under the tradename Lexan ®. The upper chamber of the housing is provided with an air inlet 16 and an air outlet 18, while the lower chamber is similarly provided with an air inlet 20 and an air outlet 22.

Arranged within the housing 10 is at least one concentrator flask 30. The housing may be configured to accommodate two or more concentrator flasks if desired. The concentrator flask 30 includes an upper solution vessel section 32 and a lower cold finger section 34. The concentrator is also preferably formed of a transparent material, for example, glass or a transparent plastic. Concentrator flasks of this type are known in the art and commercially available as microconcentrators and Kuderna Danish concentrators. If desired, the concentrator flask 30 can include graduated indications as shown in FIG. 1. In accordance with an important feature of the invention, the concentrator flask 30 is arranged within the housing 10 with the solution vessel section 32 positioned in the upper chamber 12 of the housing and the cold finger section 34 positioned in the lower chamber 14 of the housing. Preferably, the housing is provided with a dividing wall 24 which separates the upper chamber from the lower chamber, with the concentrator flask passing through the dividing wall and in sealing engagement with the wall. For example, an O-ring 25 or the like may be used to ensure sealing engagement between the flask and the dividing wall.

A reflux condenser tube 40 is arranged at the upper end of the concentrator flask. The reflux tube is also preferably formed of a transparent material such as glass or a transparent plastic. The reflux condenser tube fits on top of the concentrator flask, for example, by means of a ground joint in a manner well known in the art. Preferably, the concentrator flask and the reflux tube are held in place with the housing by means of one or more retaining springs 36 and 42 as shown in FIG. 1.

Figure 2:
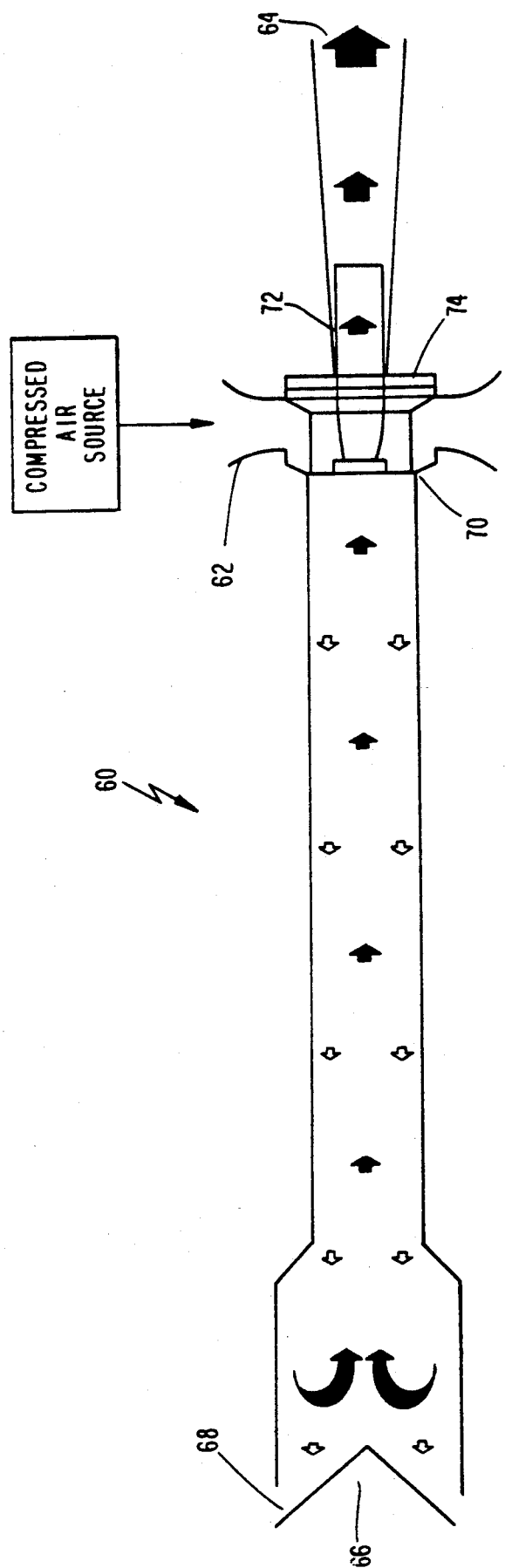
FIG. 2 is a schematic drawing of a vortex tube for use in the apparatus of the present invention.

In accordance with an additional important feature, the apparatus further includes a vortex tube 50 having a cold air outlet 52 and a hot air outlet 54. The cold air outlet 52 of the vortex tube is connected with the inlet 20 of the lower chamber of the housing while the vortex hot air outlet 54 is connected with the inlet 16 of the upper chamber of the housing. Vortex tubes are known in the art and are available commercially in a number of sizes. See, for example, Hilsch, R., *Rev. Sci. Instr.*, 1947, 18(2), 108; Blaber, M. P., *J. Sci. Instr.*, 1950, 27(6), 1968; Blatt, T. A., et al, ASME Paper 62-WA-200, 1963; Vortec Corporation, *A Short Course on Vortex Tubes and Application Notes*, 1984; Comassar, S., *J. Am. Soc. Naval Engrs.*, 1951, 63:1, pp. 99–108; Aronson, *Machine Design*, Dec. 9, 1976. A suitable vortex tube is also shown schematically in FIG. 2. The vortex tube 60 includes a compressed air inlet nozzle 62, a cold air outlet 64 and a hot air outlet 66. The hot air outlet is provided with a control valve 68 in order to control the flow of hot air from the vortex tube. The vortex tube includes the vortex generation chamber indicated generally by reference number 70 containing a vortex generator 72. A diaphragm 74 is also included in the vortex tube in a manner well known in the art. As is also known in the art, the vortex generator may comprise a replaceable insert with different vortex generator inserts being used to adjust the temperatures of air provided at the hot and cold outlets, respectively. Generally, vortex tubes can provide cold air at a temperature as low as −40° C. and hot air at a temperature as high as 200° C. The hot and cold outlet temperatures can be adjusted by use of the hot air outlet control valve 68 and/or replaceable vortex generator inserts 72. In the present apparatus, the temperatures of the cooler air and the hotter air supplied by the vortex tube to the lower and upper chambers, respectively, of the housing are sufficient to induce the evaporative separation of the liquid sample contained in the concentrator flask and to thermally induce transport or migration of the solute into the cold finger.

It is often desirable to carefully monitor and control the temperature of the upper chamber since this temperature determines the solvent evaporation rate. Accordingly, the apparatus may further include a temperature measuring device in the upper chamber. The temperature measuring device may comprise a glass thermometer, a thermocouple, a thermistor or any other means known in the art. While the lower chamber may also be provided with a temperature measuring device, the lower chamber temperature is generally not as important in controlling the solvent evaporation rate. The lower chamber cooling of the cold finger section of the concentrator flask prevents bumping and helps to induce a concentration gradient driving the solute to the cold finger, i.e., thermal transport of the solute. The lower chamber cooling also prevents decomposition of sensitive solutes in the cold finger section.

The apparatus and method of the invention are advantageous in that the apparatus contains no moving parts and does not require electricity for heat generation. This greatly enhances the safety of the concentration procedure. Additionally, when the housing and concentrator flask are formed of a transparent material, the apparatus allows good visibility of the sample solution during the entire concentration process. This in turn allows the operator to more carefully monitor the concentration process.

The concentrator apparatus and method of the invention have been employed to concentrate natural products such as beta-carotene and taxol and to separate environmental samples containing polychlorinated biphenols. In this regard, the previously discussed safety features demonstrate that the present apparatus and method are particularly suitable for use with hazardous materials and/or for use by personnel having limited laboratory training.

The preceding description is set forth to illustrate specific embodiments of the invention and is not intended to limit the scope of the apparatus and method of the invention. Additional embodiments and advantages within the scope of the claimed invention will be apparent to one of ordinary skill in the art.

What is claimed is:

1. Apparatus for the evaporative concentration of a liquid sample, comprising: a housing including an upper chamber and a lower chamber; a concentrator flask including an upper solution vessel section and a lower cold finger section, the concentrator flask being arranged within the housing with the solution vessel section positioned in the upper chamber and the cold finger section positioned in the lower chamber; a reflux condenser tube arranged at the upper end of the concentrator flask; and a vortex tube having an air inlet, a cold air outlet and a hot air outlet, the cold air outlet being connected with an inlet to the lower chamber of the housing and the hot air outlet being connected with an inlet to the upper chamber of the housing; and a source of compressed air connected the inlet of the vortex tube.

2. Apparatus as defined by claim 1, wherein the housing includes a wall dividing the upper and lower chambers, and the concentrator flask passes through the dividing wall and is in sealing engagement with the wall.

3. Apparatus as defined by claim 1, wherein the housing is provided with an air outlet in the upper chamber and an air outlet in the lower chamber.

4. Apparatus as defined by claim 1, wherein the housing is made of a transparent plastic material.

5. Apparatus as defined by claim 1, further including retaining springs for holding the concentrator flask in place in the housing.

6. Apparatus as defined by claim 1, further including retaining springs for holding the reflux tube in place on the concentrator flask.

7. Apparatus as defined by claim 1, wherein the upper chamber is provided with a temperature measuring device.

8. Apparatus as defined by claim 1, wherein the vortex tube includes a removable vortex generator insert.

9. Apparatus as defined by claim 1, wherein the vortex tube hot air outlet includes a valve for adjusting the flow of air therethrough.

10. A method for concentrating a liquid sample, comprising providing a liquid sample to be concentrated in a concentrator flask including an upper solution vessel section and a lower cold finger section, the concentrator flask being arranged within a housing with the solution vessel section positioned in an upper chamber of the housing and the cold finger section positioned in a lower chamber of the housing, and a reflux condenser tube being arranged at the upper end of the concentrator flask; connecting a vortex tube having a cold air outlet and a hot air outlet to the housing, the cold air outlet supplying cooler air to an inlet to the lower chamber of the housing and the hot air outlet supplying hotter air to an inlet to the upper chamber of the housing, the temperatures of the cooler air and the hotter air being sufficient to induce evaporative separation of the liquid sample.

* * * * *